Nov. 22, 1966 D. H. PERKINS Plant Pat. 2,686

CARNATION PLANT

Filed Sept. 22, 1965

WITNESS
SAMUEL H. GROVE

INVENTOR.
DANA H. PERKINS
BY Rummler & Snow
ATTYS.

United States Patent Office

Plant Pat. 2,686
Patented Nov. 22, 1966

2,686
CARNATION PLANT

Dana H. Perkins, 323 Jefferson St., Lapeer, Mich.

Filed Sept. 22, 1965, Ser. No. 489,446
1 Claim. (Cl. Plt.—70)

Figures 1, 2, 3:
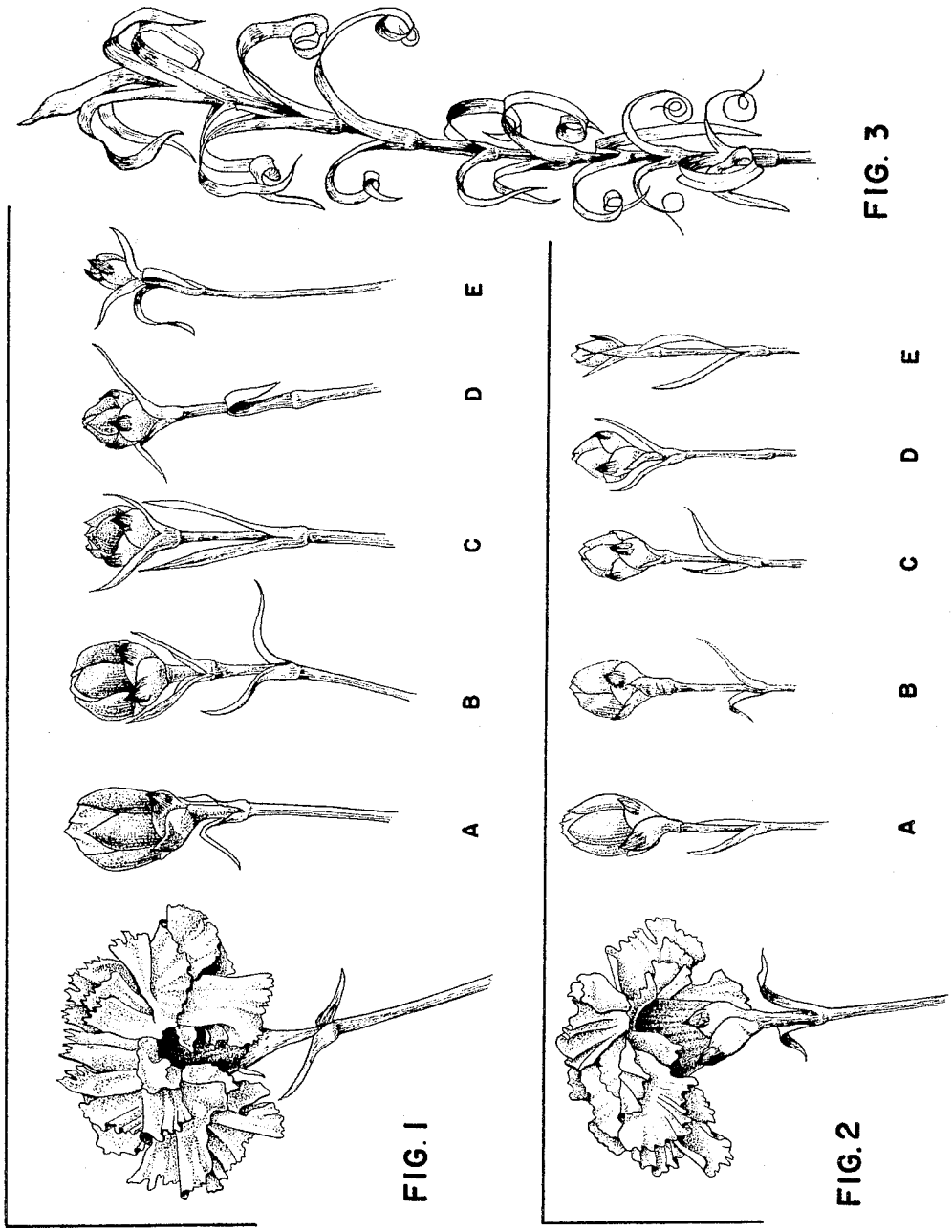

This disclosure concerns a new and improved variety of carnation plant discovered by me at my greenhouse in Lapeer, Michigan. The new variety originated as a sport of a carnation plant believed to be Peterson's Pink Sim (unpatented) and was noted to have an unusually heavy stem, for plants grown in the northern parts of the United States, and an exceptionally large white flower produced from a comparatively large, rather globose, bud. The large white bloom and strong stem, being of particular commercial advantage, prompted my propagating this sport by cuttings; and my propagation of the plant through several generations, has proved that its new and distinguishing characteristics hold true and are firmly fixed.

Continued propagation of the new variety by cuttings has been carried on at my greenhouse at Lapeer, Michigan, and I have found that the new plant, while generally similar to the White Sim varieties in color and foliage, is much stronger and more hardy than the other while carnation plants grown in this area.

It is known that the low light conditions prevailing in the northern Midwestern United States during late fall and winter are particularly conducive to weak-stemmed carnation plants. In spite of this, however, the above propagules invariably embody the excellent stem diameter and the strength of the original sport, although grown during adverse mid-winter conditions, thus indicating the possibility of competing favorably in the commercial markets with the carnation producing areas of the United States which have a higher light intensity.

In the accompanying drawings:

FIGURE 1 illustrates several stages of maturing bud and the resulting blossom of my new variety of carnation plant.

FIG. 2 is a similar view, showing buds and a blossom of a typical White Sim variety, grown in substantially side by side relation with the new variety, and under identical conditions, the correspondingly designated buds and the blossoms being of substantially the same stages of maturity as those of FIG. 1, and being drawn to the same scale for size comparison purposes; and FIG. 3 is a fragmentary view, showing a portion of the lower end of the stem of my new variety.

The following is a detailed description of my new variety of carnation plant, as based upon observations of specimens of the plant, as grown at Lapeer, Michigan:

THE PLANT

Origin: Sport of a Sim variety believed to be Peterson's Pink Sim (unpatented).
Classification: *Dianthus caryophyllus longicaulis.*
Form: Erect and branching bush.
Height: Averages 3 to 6 inches taller than average Sim varieties.
Growth: Vigorous and strong, sturdy and upright.
Foliage: Erect and very strong stems with smooth, striate, tightly curled leaves appearing at intervals along the stem. Leaf size: 9.5 to 11.5 cm. long and 1.15 to 1.5 cm. wide at center of leaf. Leaves and stem are glaucous.

Form: Widely elliptic to globose.
Size: Very large. 3.02 to 3.07 cm. long; 2.00 to 2.5 cm. in diameter.
Color: Glaucous.
Sepals: Broadly spear-shaped, with acuminate teeth and hooded over the young bud. Color: Outside—glaucous; inside—lighter than outside, silver glaucous pubescence.
Calyx: Funnel shaped (syusepalous), smooth in aspect and large in size, averaging 3.1 to 3.4 cm. in length and 2.4 to 2.7 cm. wide.

THE FLOWER

Blooms: Continuously. Under cultural conditions blooming can be recurrent.
Size: Very large. 9.7 to 10.1 cm. in diameter and 5.4 to 6.4 cm. in depth from base of bud to crown.
Borne: In clusters. Commercially disbudded.
Shape: High center. Changing later to become more globose, being round and rising in center.
Petalage: 54 to 59 V-shaped, sharp toothed, and contiguously arranged petals.
*Color.*—Petals—white with greenish color at base. Flowers occasionally have splashes of scarlet.
*Petaloids.*—Approximately 8 to 10. Variable in size but smaller than petals—2.05 to 5.00 cm. long—and of white color.
Peduncle: Sturdy, upright and of glaucous coloring.
Fragrance: Clove-like. More fragrant than Sim varieties.
Lasting quality: Similar to Sim varieties, both as cut flowers and on the plant.

GENITAL ORGANS

Stamens: Anthers; 0.15 to 0.20 cm. long, in cyclic arrangement. Normally 10 in number but sometimes modified or aborted. Filaments: White in color, 1.80 to 2.0 cm. long.
Pollen: Pale yellow in color.
Pistil: One, 3 to 5 locules. Style 2.5 to 3.5 cm. long.
Stigmas: White in color.
Characteristics of ovaries: Central placentation.

FRUIT

Fertile, pear shaped and of pale green color at maturity.

The principal distinguishing characteristics of this new variety of carnation plant reside in the large size (diameter) of the stem or peduncle, the globose shape and large size of the bud prior to opening, and the large size of the flower compared to carnation varieties grown in a similar locale.

In this regard the following tables are illustrative of bud size and stem size of the new variety as compared with other locally grown commercial varieties of carnations.

Table I shows the comparative stem diameters of my new variety and typical plants of Alaska (an unpatented sport of White Sim) and Solred (unpatented), a Red Sim variety, of the same stage of maturity and grown under identical conditions, the measurements being taken at five corresponding nodes along the respective stems and excluding the leaf sheath. Table II is a comparison of the mature bud widths of the same three varieties, the measurements being taken at 1 cm., 2 cm., and 3 cm., upwardly from the base of the respective buds. Solred is believed to be typical of most Sim varieties in size and form.

*Table I*

STEM DIAMETER (cm.)

| | Michigan Monarch | Alaska | Solred |
|---|---|---|---|
| 1st Node | 0.54 | 0.40 | 0.35 |
| 2nd Node | 0.61 | 0.50 | 0.40 |
| 3rd Node | 0.80 | 0.50 | 0.45 |
| 4th Node | 0.89 | 0.50 | 0.45 |
| 5th Node | 0.93 | 0.55 | 0.45 |

*Table II*

BUD WIDTH

| Distance from base of bud | Michigan Monarch | Alaska | Solred |
|---|---|---|---|
| 1 cm | 1.93 | 1.90 | 1.90 |
| 2 cm | 2.55 | 2.15 | 2.22 |
| 3 cm | 1.75 | 1.70 | 1.60 |

The pronounced elliptic to globose form of the bud of my new variety, prior to opening, is a distinct difference in character from the long-tapering form of bud that is common to other carnation varieties presently grown for commercial purposes. Also, the large size of the bud of my new variety produces a very large and full blossom which is extremely advantageous from the commercial viewpoint.

Having thus described and illustrated my new variety of carnation plant, I claim:

A new and distinct variety of carnation plant, substantially as herein shown and described, characterized as to novelty by its large, strong and upright stem; the unique shape and large size of its bud; the large size and full shape of its white flower; and its vigorous growth habit which produces its distinctive characteristics of size and form in areas of low light intensity and relatively severe winter conditions.

No references cited.

ABRAHAM G. STONE, *Primary Examiner.*

R. E. BAGWILL, *Assistant Examiner.*